(12) United States Patent
Ohno

(10) Patent No.: US 8,697,309 B2
(45) Date of Patent: Apr. 15, 2014

(54) PROTON CONDUCTOR AND FUEL CELL USING THE SAME

(75) Inventor: Hiroyuki Ohno, Tokyo (JP)

(73) Assignees: Nissan Motor Co., Ltd., Kanagawa (JP); Hiroyuki Ohno, Tokyo (JP)

( * ) Notice: Subject to any disclaimer, the term of this patent is extended or adjusted under 35 U.S.C. 154(b) by 622 days.

(21) Appl. No.: 11/574,699

(22) PCT Filed: Sep. 1, 2005

(86) PCT No.: PCT/JP2005/015988
§ 371 (c)(1),
(2), (4) Date: Mar. 5, 2007

(87) PCT Pub. No.: WO2006/025482
PCT Pub. Date: Mar. 9, 2006

(65) Prior Publication Data
US 2007/0231647 A1    Oct. 4, 2007

(30) Foreign Application Priority Data
Sep. 3, 2004 (JP) ................................ 2004-256869

(51) Int. Cl.
*H01M 8/02* (2006.01)
(52) U.S. Cl.
USPC ........................................................ 429/498
(58) Field of Classification Search
USPC ........................................................ 429/30
See application file for complete search history.

(56) References Cited

U.S. PATENT DOCUMENTS

| 6,576,159 B1 | 6/2003 | Michot et al. |
| 2003/0052310 A1 | 3/2003 | Michot et al. |
| 2003/0087151 A1 * | 5/2003 | Hamrock ............... 429/188 |
| 2004/0057835 A1 | 3/2004 | Kirby |
| 2005/0211292 A1 * | 9/2005 | Chittibabu et al. ........... 136/263 |
| 2005/0221193 A1 * | 10/2005 | Kinouchi et al. ............. 429/306 |
| 2006/0263661 A1 | 11/2006 | Takizawa et al. |

FOREIGN PATENT DOCUMENTS

| EP | 0 850 932 A1 | 7/1998 | |
| JP | 9-153371 A | 6/1997 | |
| JP | 2000-251906 A | 9/2000 | |
| JP | 2003-123791 | 4/2003 | |
| JP | 2003-242996 A | 8/2003 | |
| JP | 2004-220837 A | 8/2004 | |
| JP | 2005-166598 A | 6/2005 | |
| JP | 2005-228588 A | 8/2005 | |
| JP | 2005228588 A * | 8/2005 | |
| WO | WO 03/035609 A1 | 5/2003 | |
| WO | WO 04001771 A1 * | 12/2003 | ............ H01M 10/40 |

OTHER PUBLICATIONS

Communication (Supplementary European Search Report) in EP Appln No. 05776899.6 dated Oct. 29, 2010.
Ohno, et al. "A new type of polymer gel electrolyte: zwitterionic liquid/polar polymer mixture", Electrochimica Acta, 2003, vol. 48, pp. 2079-2083.

* cited by examiner

*Primary Examiner* — Barbara Gilliam
*Assistant Examiner* — Stephan Essex
(74) *Attorney, Agent, or Firm* — Foley & Lardner LLP

(57) ABSTRACT

The present invention is to provide a novel proton conductor comprising a zwitterionic type ionic liquid that can solve a problem of a complicated and enlarged system caused by installing a system of a humidifying device, a recovering device and a resupplying device that are necessary to keep proton transportation stably in an operation environment of a fuel cell. A proton conductor comprising an ionic liquid having a zwitterion wherein an anion and a cation coexist in one molecule, and a proton donor is provided.

3 Claims, 3 Drawing Sheets

METHOD FOR SYNTHESIZING A ZWITTERIONIC TYPE IONIC LIQUID

DIAGRAM ILLUSTRATING CONFIRMATION OF STRUCTURE OF ZWITTERIONIC TYPE IONIC LIQUID USING $^1$H NMR

STRUCTURAL FORMULA OF HTFSI (PROTON DONOR)

PROTON CONDUCTOR AND FUEL CELL USING THE SAME

TECHNICAL FIELD

The present invention relates to a proton conductor containing a novel ionic liquid, and a fuel cell using the same.

BACKGROUND ART

A fuel cell using a proton conductor includes a proton-exchange membrane fuel cell using a fluorine-based polymer membrane represented by Nafion (registered trademark) (it is same, hereinafter) as an electrolyte, and a phosphoric acid fuel cell.

In the case of Nafion (registered trademark), a proton is transported by utilizing water contained in a fluorine-based polymer membrane, but the water gradually evaporates at an operating temperature (60 to 80° C.) of a proton-exchange membrane fuel cell, which causes the fluorine-based polymer membrane to dry with time and thus lowers the proton conductivity. Therefore, in a conventional proton-exchange membrane fuel cell system using Nafion (registered trademark), because water is necessary to be present in the system for attaining high proton conductivity, a humidifying device for humidifying a feed gas is required. Further, because the amount of water to be stored in the humidifying device can be decreased by recovering water contained in a gas exhausting from a fuel cell, it is desirable to add a device for recovering water from the exhaust gas from a fuel cell. However, in the case where a fuel cell serves as an energy source for mobile equipment, such a device for humidifying a feed gas requires to be accompanied by a device for precisely controlling an amount of the humidifying water depending on a load change of the fuel cell and also a device for resupplying water for humidifying connecting with a device for recovering the water from the exhaust gas, which causes a problem of a complicated and enlarged system. In the case of a motor vehicle, there has been a risk that water contained in a fluorine-based polymer membrane freezes (in cold districts and soon) or evaporates (under the scorching sun in summer, and so on) depending on ambient conditions even when a fuel cell is not operated.

In the case of a phosphoric acid fuel cell, a proton is transported by phosphoric acid impregnated in a porous materials such as SiC (silicon carbide). However, because a phosphoric acid has a vapor pressure at an operating temperature (approximately 200° C.) of the phosphoric acid fuel cell, a liquid is necessary to be supplied. Such a system for recovering and resupplying a vaporized phosphoric acid as described in, for example, JP-A-9(1997)-153,371 is necessary. This has posed a problem of a complicated and enlarged system.

DISCLOSURE OF INVENTION

It is an object of the present invention to provide a novel proton conductor containing a zwitterionic type ionic liquid that can solve a problem in a complicated and enlarged system as a whole caused by installing a system of a humidifying device, a recovering device and a resupplying device that are necessary to keep proton transportation stably in an operation environment of a fuel cell.

It is another object of the present invention to provide a fuel cell using the proton conductor.

The above objects can be attained by a proton conductor containing an ionic liquid having a zwitterion wherein an anion and a cation coexist in one molecule, and a proton donor.

According to the proton conductor of the present invention, since a vapor pressure of the proton conductor of the present invention is extremely low at an operating temperature of a fuel cell, a stable proton conductor that a conductor does not scatter can be realized. In addition, an ionic liquid contained in the proton conductor of the present invention is not attracted to one of the electrodes, to induce selective transportation of a proton (hydrogen ion: $H^+$) given by a proton donor contained in the proton conductor of the present invention, because a cation and an anion coexist in one molecule constituting the ionic liquid.

According to a fuel cell using the proton conductor of the present invention, since the conductor does not scatter even when the fuel cell is operated, it is possible to omit a system for recovering and resupplying a scattering conductor.

BEST MODE FOR CARRYING OUT THE INVENTION

The mode for carrying out the present invention will be described hereinafter.

The proton conductor according to the present invention comprises an ionic liquid having a zwitterion wherein an anion and a cation coexist in one molecule, and a proton donor.

As an ionic liquid, an ethylmethylimidazolium salt of an ethylmethylimidazolium cation with $BF^-_4$, $PF^-_6$, $(CF_3SO_2)_2N^-$ or the like has been well-known. These ordinary ionic liquids can solve a problem in scattering when they are used as a proton conductor of a fuel cell, because they have little vapor pressure. Since these ordinary ionic liquids are not designed so as to give a field for making a proton ($H^+$) exist stably, however, an anion and a cation constituting the ionic liquid are attracted along a potential gradient formed between electrodes and move to the vicinity of each electrode. Accordingly, electric charge is locally present and electrode characteristics would be drastically deteriorated, which makes these ordinary ionic liquids difficult to be used as a proton conductor.

Consequently, in the present invention, an ionic liquid containing a zwitterion wherein a cation and an anion coexist in one molecule (hereinafter referred to simply as "zwitterionic type ionic liquid") has been newly invented, based on an idea that a proton can be selectively transported by repressing movement of an ionic liquid itself. In the zwitterionic type ionic liquid, both of a cation and an anion constituting the ionic liquid are fixed in a molecule and thus are repressed from movement along a potential gradient and fixed between both electrodes. Therefore, a high-speed ion-conducting path, which allows only desired ion to move, can be formed. It is advantageous that there is no deterioration of electric characteristics caused by uneven distribution of electric charge. Further, since the ionic liquid containing a zwitterion of the present invention does not have a proton (hydrogen-ion source) in the molecule, it can not transport a hydrogen ion in an electrolyte when used for an electrolyte (proton conductor) of a fuel cell. Accordingly, $H^+$ (proton) is necessary to be added by mixing a proton donor (protonic acid). Because such a proton donor itself has vapor pressure at an operating temperature of a fuel cell, it has been easily predicted that, in case of a liquid type proton conductor formed by mixing the above ionic liquid with a proton donor, the proton donor would evaporate to deteriorate proton conductivity like a conventional manner. However, as shown in FIG. 3 in the Example described later, in a combination of a novel zwitterionic type ionic liquid with a proton donor, a phenomenon that a proton donor does not evaporate even at an operating temperature of a fuel cell has been found to generate. Based on such findings, a novel proton conductor of the present invention that does not have vapor pressure even at an operating temperature of a fuel cell and does not require a complicated system has been completed.

The proton conductor of the present invention will be described in detail hereinafter.

The ionic liquid to be used for the proton conductor of the present invention comprises a zwitterion wherein an anion and a cation coexist in one molecule, but may contain an ordinary type ionic liquid and the like wherein an anion and a cation do not combine, as well as the zwitterion.

The above-described zwitterionic type ionic liquid has the characteristics such as (1) little vapor pressure, (2) ionic but low viscous, (3) thermal resistance, and broad temperature range in liquid phase, (4) extremely high ion conductivity derived from so high ion density as to be unable to attain by an ordinary solution and high ion mobility, and (5) good solvent for various salts. Further, both of an anion and a cation constituting the ionic liquid are fixed in the molecule, and the cation or the anion of ionic liquid do not move separately along a potential gradient and these ions (electric charges) are not unevenly distributed around electrodes, so as to not to deteriorate electric characteristics during the use. It is also advantageous that a high-speed ion-conducting path (electrolyte membrane or proton conductor), which allows a hydrogen ion to move, can be formed by adding a hydrogen ion with a proton donor mixed to the ionic liquid. Further, by mixing with a proton donor having vapor pressure with the ionic liquid, effects of repressing evaporation of the proton donor can be effectively expressed. In this case, the expression "effects can be effectively expressed" means that the effects can be effectively expressed at an operating temperature range of a fuel cell, and effects of repressing evaporation of the proton donor can be maintained even when the proton donor is blended in such an amount as to ensure the ion conductivity required for a proton conductor of a fuel cell. When a blending ratio of a proton donor is unduly high, effects of repressing evaporation of the proton donor by interaction between the proton donor and a zwitterionic type ionic liquid would be reduced, allowing an excessive proton donor to evaporate. However, after the excessive proton donor is lost by evaporation, effects of repressing evaporation of the proton donor by interaction between the proton donor and the zwitterionic type ionic liquid would be recovered (expressed) leading to termination of evaporation of the proton donor and thus the ion conductivity does not lower beyond a certain level. Further, since a blending ratio of a zwitterionic type ionic liquid and a proton donor in which effects of repressing evaporation of the proton donor can be maintained can be confirmed in advance by determining a rate of thermogravimetry reduction as shown in FIG. 3, the evaporation of such an excessive proton donor can be prevented without any difficulty.

The zwitterionic type ionic liquid wherein an anion and a cation coexist in one molecule, which has been created by the present inventor, shows different behaviors (characteristics) from a conventional ionic liquid when used as a proton conductor as described above. However, basic characteristics (the above (1) to (5)) thereof, are similar to those of an ordinary ionic liquid. Such zwitterionic type ionic liquid is not especially limited, and a desired zwitterionic type ionic liquid such as of a imidazolium salt, a pyridinium salt, and an ammonium salt can be synthesized (designed) by a production method (synthesis method) which will be described later. Examples of the suitable zwitterionic type ionic liquids will be described hereinbelow.

A cation moiety of the zwitterionic type ionic liquid may be preferably an onium cation.

The onium cation is not especially limited, so long as it be a cation having at least one organic group formed by coordinating a cation type atomic group to a compound containing an element having an isolated electron pair such as nitrogen, sulfur, oxygen, phosphorus, selenium, tin, iodine and antimony. Examples of an organic onium ion that can be used in the present invention include symmetric ammonium cations such as a tetramethylammonium cation, tetraethylammonium cation and tetrapropylammonium cation; ammonium cations, in which the number of carbon atoms of the shortest substituent is not less than 50% and less than 100% of the number of carbon atoms of the longest substituent (hereinafter, may be referred to as pseudo symmetric), such as an ethyltrimethylammonium cation, vinyltrimethylammonium cation, triethylmethylammonium cation, triethylpropylammonium cation, diethyldimethylammonium cation, tributylethylammonium cation, triethylisopropylammonium cation, N,N-dimethylpyrrolidinium cation, N-methyl-N-ethylpyrrolidinium cation and triethylmethoxymethylammonium cation; asymmetric ammonium cations such as a trimethylpropylammonium cation, trimethylisopropylammonium cation, butyltrimethylammonium cation, allyltrimethylammonium cation, hexyltrimethylammonium cation, octyltrimethylammonium cation, dodecyltrimethylammonium cation, triethylmethoxyethoxymethylammonium cation and dimethyldipropylammonium cation; divalent ammonium cations such as a hexamethonium cation; symmetric imidazolium cations such as a 1,3-dimethylimidazolium cation, 1,3-diethylimidazolium cation, 1,3-dipropylimidazolium cation and 1,3-dibutylimidazolium cation; asymmetric imidazolium cations such as an 1-ethyl-3-methylimidazolium cation, 1-methyl-3-propylimidazolium cation, 1-isopropyl-3-propylimidazolium cation and 1-tert-butyl-3-isopropylimidazolium cation; pyridinium cations such as an N-ethylpyridinium cation and N-butylpyridinium cation; symmetric sulfonium cations such as a trimethylsulfonium cation, triethylsulfonium cation and tributylsulfonium cation; pseudo symmetric sulfonium cations such as a diethylmethylsulfonium cation; asymmetric sulfonium cations such as a dimethylpropylsulfonium and dimethylhexylsulfonium; symmetric phosphonium cations such as a tetramethylphosphonium cation, tetraethylphosphonium cation, tetrapropylphosphonium cation, tetrabutylphosphonium cation, tetraoctylphosphonium cation and tetraphenylphosphonium cation; pseudo symmetric phosphonium cations such as a trimethylethylphosphonium cation and triethylmethylphosphonium cation; asymmetric phosphonium cations such as a hexyltrimethylphosphonium cation and trimethyloctylphosphonium cation; and the like. In addition, both of the onium cation specifically exemplified above and an onium cation represented by the following structural formula 1' and structural formula 1 are exemplified without distinguishing each other. Accordingly, the onium cation exemplified above may be included in the onium cation represented by the following structural formula 1' and structural formula 1, but the present invention is not limited thereby at all.

The organic onium ion that can be used in the present invention includes, but is not limited thereto, one represented by the following structural formula 1':

(Formula 1)

and one represented by the structural formula 1 to be shown later.

In the above structural formula 1', $R^7$, $R^8$, $R^9$ and $R^{10}$, independently, represent an alkyl group, an aryl group, a heterocyclic group or an aralkyl group. These $R^7$, $R^8$, $R^9$ and $R^{10}$ may have a substituent or a hetero atom in the structure thereof. In addition, $R^7$, $R^8$, $R^9$ and $R^{10}$ may be bound with each other, to form a ring. Further, $R^7$, $R^8$, $R^9$ and $R^{10}$ of an adjacent cation may be bound with each other, to form a polymer-like structure.

The alkyl group includes straight or branched-chain alkyl groups having 1 to 30 carbon atoms, such as methyl group, ethyl group, n-propyl group, isopropyl group, n-butyl group, isobutyl group, sec-butyl group, tert-butyl group, pentyl group, hexyl group, heptyl group, octyl group, nonyl group and decyl group.

The aryl group includes phenyl group, naphthyl group, toluyl group and xylyl group.

The aryl group may have one or plural substituents such as halogen atoms (fluorine atom, chlorine atom, bromine atom and iodine atom), hydroxyl group, alkoxy group (methoxy group, ethoxy group, propoxy group, butoxy group and the like), carboxyl group, acetyl group, propanoyl group, thiol group, alkylthio group (methylthio group, ethylthio group, propylthio group, butylthio group and the like), amino group, alkylamino group and dialkylamino group.

The heterocyclic group includes pyridyl group, thienyl group, imidazolyl group, pyrazolyl group, oxazolyl group, isooxazolyl group, pyrrolidinyl group, piperazinyl group and morpholinyl group and the like.

The aralkyl group includes benzyl group and phenethyl group and the like.

In addition, the above $R^7$, $R^8$, $R^9$ and $R^{10}$ may be bound with each other in one molecule to form a ring like pyrrolidinium or piperidinium.

Further, the $R^7$, $R^8$, $R^9$ and $R^{10}$ may be bound with $R^7$, $R^8$, $R^9$ and $R^{10}$ of an adjacent another cation to form a chain.

In addition, one the $R^7$, $R^8$, $R^9$ and $R^{10}$, which binds with an anion moiety to be described later, is a divalent group that is obtained by taking one hydrogen atom away from a monovalent group as shown above.

An onium cation represented by the following structural formula 1:

(Formula 2)

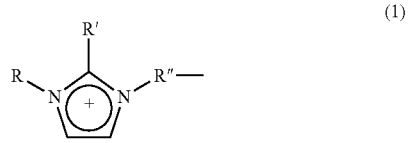

is more preferable.

In the above formula, R represents a hydrogen atom, an alkyl group having 1 to 18 carbon atoms, an aryl group, a heterocyclic group or an aralkyl group, preferably a hydrogen atom or an alkyl group having 1 to 18 carbon atoms, more preferably an alkyl group having 1 to 8 carbon atoms. R' represents a hydrogen atom, an alkyl group having 1 to 18 carbon atoms, an aryl group, a heterocyclic group or an aralkyl group, preferably a hydrogen atom or an alkyl group having 1 to 18 carbon atoms, more preferably a hydrogen atom or an alkyl group having 1 to 8 carbon atoms. R" represents an alkylene group having 1 to 18 carbon atoms, an arylene group, a heterocyclic group or an aralkylene group, preferably an alkylene group having 1 to 18 carbon atoms, more preferably an alkylene group having 1 to 8 carbon atoms. R, R' and R" may have a substituent, a hetero atom in the structure thereof. In addition, R, R' and R" may be bound with each other to form a ring. Further, R, R' and R" of an adjacent cation may be bound with each other, to form a polymer-like structure.

The alkyl group having 1 to 18 carbon atoms includes straight or branched-chain alkyl groups having 1 to 18 carbon atoms, such as methyl group, ethyl group, n-propyl group, isopropyl group, n-butyl group, isobutyl group, sec-butyl group, tert-butyl group, pentyl group, hexyl group, heptyl group, octyl group, nonyl group and decyl group.

The aryl group includes phenyl group, naphthyl group, toluyl group and xylyl group.

The heterocyclic group includes pyridyl group, thienyl group, imidazolyl group, pyrazolyl group, oxazolyl group, isooxazolyl group, pyrrolidinyl group, piperazinyl group and morpholinyl group.

The aralkyl group includes benzyl group and phenethyl group.

The R" group, which binds with an anion moiety to be described later, is a divalent group that is obtained by taking one hydrogen atom away from a monovalent R group shown above.

Specifically, the alkylene group having 1 to 18 carbon atoms includes straight or branched-chain group having 1 to 18 carbon atoms such as methylene group, ethylene group, propylene group, butylene group, pentylene group, hexylene group, heptylene group, octylene group, nonylene group and decylene group.

The arylene group includes phenylene group, naphthylene group, toluylene group and xylylene group.

The heterocyclic group includes pyridylene group, thienylene group, imidazolylene group, pyrazolylene group, oxazolylene group, pyrrolidinylene group, piperazinylene group and morpholinylene group.

The aralkylene group includes benzylene group and phenethylene group.

The R, R' and R" may be bound with each other in one molecule to form a ring like pyrrolidinium or piperidinium.

The R, R' and R" may be bound with R, R' and R" of an adjacent another cation to form a chain.

Further, so long as characteristics of a zwitterionic type ionic liquid of the present invention be not impaired, R, R' and R" may have a substituent or a hetero atom in the structure thereof. Such substituent includes halogen atoms (fluorine atom, chlorine atom, bromine atom and iodine atom), hydroxyl group, alkoxy group (methoxy group, ethoxy group, propoxy group, butoxy group and the like), carboxyl group, acetyl group, propanoyl group, thiol group, alkylthio group (methylthio group, ethylthio group, propylthio group, butylthio group and the like), amino group, alkylamino group and dialkylamino group and the like. R, R' and R" may have one or plural of these substitutes.

The anion moiety of the zwitterion selected from the group represented by the following structural formula 2:

(Formula 3)

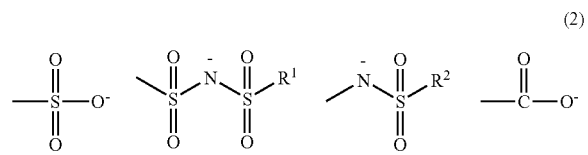

(2)

may be preferably used.

Here, in the above formula, $R^1$ and $R^2$ independently represent a substituted or unsubstituted monovalent hydrocarbon group or a fluorocarbon group having 1 to 5 carbon atoms, but are not limited thereto.

Although the $R^1$ and $R^2$ are not especially limited, so long as that they be independently represent a substituted or unsubstituted monovalent hydrocarbon group or a fluorocarbon group ($—(CF_2)_nF$) having 1 to 5 carbon atoms, they are preferably a halogen atom or a halogenated hydrocarbon, particularly preferably a fluorine-substituted hydrocarbon group in terms of high resistance to oxidation. The fluorine-substituted hydrocarbon group is specifically exemplified by fluoroalkyl groups such as trifluoromethyl group, pentafluoroethyl group, heptafluoropropyl group, nonafluorobutyl group, heptafluoroisopropyl group, nonafluoroisobutyl group, 2,2,2-trifluoroethyl group and 1,1-difluoroethyl group; fluoroaryl groups such as pentafluorophenyl group and 2,4,6-trifluorophenyl group; and fluoroaralkyl groups such as heptafluorobenzyl group and 1,1-difluorobenzyl group. Among these, a straight or branched-chain perfluoroalkyl group having 1 to 6 carbon atoms, a perfluorophenyl group and a perfluoroaralkyl group having 7 to 9 carbon atoms are particularly preferable in terms of high ion conductivity. Further, the $R^1$ and $R^2$ are preferably a group capable of attracting electron and having 1 to 6 carbon atoms (also called "electron attractive group") or a group having an electron attractive group in terms of high ion conductivity of the onium salt. The term "electron attractive group" used herein is referred to a group having a larger substituent constant in Hammett's rule than that of a hydrogen atom. The preferable electron attractive group and group having an electron attractive group are specifically exemplified by fluorinated hydrocarbon groups (hydrocarbon group substituted by fluorine) including fluoroalkyl groups such as trifluoromethyl group, pentafluoroethyl group, heptafluoropropyl group, nonafluorobutyl group, heptafluoroisopropyl group, nonafluoroisobutyl group, 2,2,2-trifluoroethyl group and 1,1-difluoroethyl group, fluoroaryl groups such as pentafluorophenyl group and 2,4,6-trifluorophenyl group, and fluoroaralkyl groups such as heptafluorobenzyl group and 1,1-difluorobenzyl group; acyl groups such as formyl group, acetyl group, propionyl group, butyryl group, isobutyryl group, valeryl group, isovaleryl group, pivaloyl group and lauroyl group; fluorinated acyl groups (acyl group substituted by fluorine) such as trifluoroacetyl group, 2,2-difluoropropionyl group, perfluoropropionyl group, perfluorobutyryl group, perfluoroisobutyryl group and perfluorovaleryl group; substituted acyl groups having a substituent other than fluorine such as methoxycarbonyl group, ethoxycarbonyl group, tert-butoxycarbonyl group, trifluoromethoxycarbonyl group, perfluoroethoxycarbonyl group and perfluoro-tert-butoxycarbonyl group; sulfonyl groups such as methanesulfonyl group, ethanesulfonyl group, propanesulfonyl group and tert-butanesulfonyl group; fluorinated sulfonyl groups (sulfonyl group substituted by fluorine) such as trifluoromethanesulfonyl group, pentafluoroethanesulfonyl group, heptafluoropropanesulfonyl group, nonafluorobutanesulfonyl group, heptafluoroisopropanesulfonyl group, nonafluoroisobutanesulfonyl group, 2,2,2-trifluoroethanesulfonyl group and 1,1-difluoroethanesulfonyl group; and fluorinated benzenesulfonyl groups such as pentafluorobenzenesulfonyl group and 2,4,6-trifluorobenzenesulfonyl group. The fluorine-substituted hydrocarbon group specifically exemplified above and the electron attractive group or group having an electron attractive group are cited specifically without distinguishing each other. Accordingly, the fluorine-substituted hydrocarbon group specifically exemplified above may be included in the electron attractive group or the group having an electron attractive group, but the present invention is not limited thereby at all.

A proton donor to be used in the proton conductor of the present invention is not especially limited. Preferably, the proton donor is selected from the group represented by the following structural formula 3.

(Formula 4)

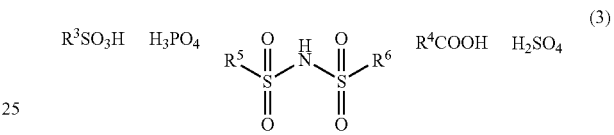

(3)

The proton donor is not limited to the above group, but may be any acid ($H^+$ donor), which may be selected as appropriate in accordance with the intended use.

The $R^3$ is a hydrocarbon group having 1 to 5 carbon atoms or a fluorocarbon group ($—(CF_2)_nF$) having 1 to 5 carbon atoms, and preferably a hydrocarbon group having 1 to 2 carbon atoms. Specific examples of $R^3$ include methyl group and ethyl group.

$R^4$ is a hydrocarbon group having 1 to 5 carbon atoms or a fluorocarbon group ($—(CF_2)_nF$) having 1 to 5 carbon atoms, and preferably a hydrocarbon group having 1 to 2 carbon atoms. Specific examples of $R^4$ include methyl group and ethyl group.

The $R^5$ and $R^6$ independently represent a substituted or unsubstituted monovalent hydrocarbon group or a fluorocarbon group ($—(CF_2)_nF$) having 1 to 5 carbon atoms. One of the $R^5$ and $R^6$ is preferably a halogen atom or a halogenated hydrocarbon group and particularly preferably a fluorine-substituted hydrocarbon group in terms of high resistance to oxidation. The fluorine-substituted hydrocarbon group is specifically exemplified by fluoroalkyl groups such as trifluoromethyl group, pentafluoroethyl group, heptafluoropropyl group, nonafluorobutyl group, heptafluoroisopropyl group, nonafluoroisobutyl group, 2,2,2-trifluoroethyl group and 1,1-difluoroethyl group; fluoroaryl groups such as pentafluorophenyl group and 2,4,6-trifluorophenyl group; and fluoroaralkyl groups such as heptafluorobenzyl group and 1,1-difluorobenzyl group. Among these, a straight or branched-chain perfluoroalkyl group having 1 to 6 carbon atoms, a perfluorophenyl group and a perfluoroaralkyl group having 7 to 9 carbon atoms are particularly preferable in terms of high ion conductivity.

The other of the $R^5$ and $R^6$ is preferably a group capable of attracting electron and having 1 to 6 carbon atoms (also called "electron attractive group") or a group having an electron attractive group in terms of high ion conductivity of the onium salt. The term "electron attractive group" used herein is referred to a group having a larger substituent constant in Hammett's rule than that of a hydrogen atom. The preferable electron attractive group and group having an electron attractive group are specifically exemplified by fluorinated hydrocarbon groups (hydrocarbon group substituted by fluorine) including fluoroalkyl groups such as trifluoromethyl group, pentafluoroethyl group, heptafluoropropyl group, nonafluorobutyl group, heptafluoroisopropyl group, nonafluoroisobutyl group, 2,2,2-trifluoroethyl group and 1,1-difluoroethyl group, fluoroaryl groups such as pentafluorophenyl group and 2,4,6-trifluorophenyl group, and fluoroaralkyl groups such as heptafluorobenzyl group and 1,1-difluorobenzyl group; acyl groups such as formyl group, acetyl group, propionyl group, butyryl group, isobutyryl group, valeryl group, isovaleryl group, pivaloyl group and lauroyl group; fluorinated acyl groups (acyl group substituted by fluorine) such as trifluoroacetyl group, 2,2-difluoropropionyl group, perfluoropropionyl group, perfluorobutyryl group, perfluoroisobutyryl group and perfluorovaleryl group; substituted acyl groups having a substituent other than fluorine such as methoxycarbonyl group, ethoxycarbonyl group, tert-butoxycarbonyl group, trifluoromethoxycarbonyl group, perfluoroethoxycarbonyl group and perfluoro-tert-butoxycarbonyl group; sulfonyl groups such as methanesulfonyl group, ethanesulfonyl group, propanesulfonyl group and tert-butanesulfonyl group; fluorinated sulfonyl groups (sulfonyl group substituted by fluorine) such as trifluoromethanesulfonyl group, pentafluoroethanesulfonyl group, heptafluoropropanesulfonyl group, nonafluorobutanesulfonyl group, heptafluoroisopropanesulfonyl group, nonafluoroisobutanesulfonyl group, 2,2,2-trifluoroethanesulfonyl group and 1,1-difluoroethanesulfonyl group; and fluorinated benzenesulfonyl groups such as pentafluorobenzenesulfonyl group and 2,4,6-trifluorobenzenesulfonyl group. The fluorine-substituted hydrocarbon group specifically exemplified above and the electron attractive group or group having an electron attractive group are cited specifically without distinguishing each other. Accordingly, the fluorine-substituted hydrocarbon group specifically exemplified above may be included in the electron attractive group or the group having an electron attractive group, but the present invention is not limited thereby at all. Introduction of such a halogen atom and a halogenated alkyl group having very strong electron-attractiveness into $R^5$ and $R^6$ is effective for easy dissociation of a hydrogen ion ($H^+$).

The structure of a salt that is a zwitterionic type ionic liquid of the present invention can be confirmed using NMR and the like as shown in the Example to be described later. Thermodynamic properties (for example, a melting point, a glass transition temperature, presence or absence of an exothermic peak in crystallization and eventually confirmation of showing with time a thermodynamically stable liquid state without crystallizing around a room temperature (30° C.)) can be determined using DSC (differential scanning calorimetry) measurement. Conductivity (ionic conductivity (s)) can be determined by measurement of complex impedance. Further, other various properties such as viscosity (η), density (ρ), glass transition temperature (Tg) determined by DSC measurement, and self-diffusion coefficient (D) determined by pulsed gradient spin-echo NMR (PGSE-NMR) can be obtained. A ratio of contribution of an ion as a carrier to conduction in the system can be estimated by computing a ratio (Haven Ratio) of mol conductivity ($\lambda_{imp}$) obtained by impedance measurement and mol conductivity ($\lambda_{diff}$) obtained by introducing a self-diffusion coefficient into Nernst-Einstein equation.

Then, a method for producing a zwitterionic type ionic liquid according to the present invention will be described by referring as an example to a synthesis method represented by the following reaction formula (4) by single stage reaction of a tertiary amine and an alkylsultone, which is one of suitable synthesis methods of a zwitterionic type ionic liquid composed of a cation moiety represented by the above structural formula 1 and an anion moiety represented by the structural formula 2, but the present invention is not limited thereto. This synthesis method has been created by present inventors. Since the method produce no by-products during synthesis, the purification process is simple, and contamination of a microion can be also prevented. In other words, since an ionic liquid dissolves a salt well, it is difficult to completely remove the salt when salt is formed as a by-product. Accordingly, the method to be described hereinbelow can be said to be extremely effective for obtaining a pure zwitterionic type ionic liquid.

(Formula 5)

(4)

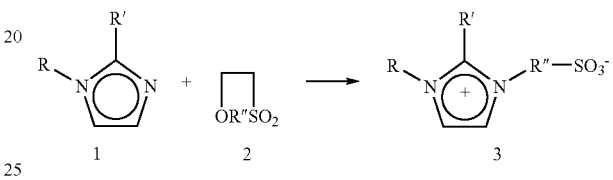

As shown by the reaction formula 4, a solution of a tertiary amine (hereinafter, referred to as "compound 1") in a solvent A is mixed with a solution of an alkylsultone (hereinafter, referred to as "compound 2") in an equimolar amount relative to the compound 1 in a solvent B at about 0 to 10° C. Then, the mixture is heated up to 10 to 30° C., and then reacted at the above temperature while being stirred under an inert-gas atmosphere for about 5 days. After stopping stirring, the solvents A and B are removed, and the residue is washed to obtain a zwitterionic type ionic liquid (hereinafter, referred to as "product 3"), which is a colorless, clear and viscous liquid.

In the above reaction, the solvent A includes acetone and the like, but is not limited thereto. The solvent B includes acetonitrile, acetone and the like, but is not limited thereto. The solvent A that can dissolve the compound 1 and the solvent B that can dissolve the compound 2 may be the same or different. When both solvents are hardly soluble or insoluble in each other, sufficient stirring is necessary during reaction.

In addition, in the above reaction, the amount of the compound 2 may be in the range of 1 to 2 moles, based on 1 mole of the compound 1. However, both compounds are preferably equimolar, because as shown by the above reaction, the reaction using the compounds 1 and 2 in equimolar amounts gives no by-products or unaltered substances, resulting in simple purification. Accordingly, the amount of the compound 2 is preferably used in the same molar amount as of the compound 1.

In the above reaction, the reason why the solution of the compound 1 and the solution of the compound 2 are mixed at 0 to 10° C. is to prevent undesirable reaction from proceeding during mixing. For the above reason, mixing is carried out preferably in the range of 0 to 10° C., particularly preferably at about 0° C.

Further, the reason why the temperature is raised to about 10 to 30° C. after mixing and the reaction is carried out within such a temperature range is to prevent by-product formation. For the above reason, the temperature is raised preferably to 10 to 30° C., particularly preferably to a room temperature, and then the reaction is carried out at the above temperature.

The reason why the reaction is carried out under an inert-gas atmosphere is to prevent oxidation, which is aside reaction. Although the inert-gas atmosphere includes, for example, a nitrogen atmosphere and an argon atmosphere, a nitrogen atmosphere is preferable in view of cost.

The reaction time may be a time for almost completing the reaction. The time of about 5 days is merely a rough indication, since the reaction time depends on the kinds of compounds 1 and 2 and the reaction temperature condition.

After completion of the reaction, the solvents A and B can be removed as by, for example, vacuum drying, but to which it is not limited. The residue after solvent removal can be washed with, for example, acetone, but to which it is not limited.

In the zwitterionic type ionic liquid of the present invention, a zwitterion wherein an anion and a cation coexist in one molecule of the product 3 obtained by the above synthesis method can be used as it is. However, the present invention should not be limited to the above, and an appropriate amount of another ordinary ionic liquid that is not zwitterionic, can be added, so long as effects and function of the proton conductor of the present invention and cell characteristics of a fuel cell be not impaired. Production using different amounts of the reactants 1 and 2 and a different synthesis method would allow sometime unaltered substances and by-products to remain in the product, depending on production conditions. A complicated and cumbersome purification operation can prevent such residues from contaminating the product, but increases the production cost. In such a case, the residues may be contained in the ionic liquid of the present invention within such an amount as that effects and function of the proton conductor of the present invention and cell characteristics of a fuel cell be not impaired. For this reason, the ionic liquid of the present invention has been made to contain a zwitterion wherein an anion and a cation coexist in one molecule.

Identification of the reaction product 3 obtained by the reaction and confirmation that the reaction product 3 is a zwitterionic type ionic liquid can be carried out by NMR shown in the Example described later.

Next, a method for preparing a proton conductor according to the present invention is not especially limited, and a method explained specifically in the Example described later can be used for production. That is, a zwitterion in the above zwitterionic type ionic liquid and a proton donor are weighed so as to give a predetermined molar ratio, and if necessary, an appropriate amount of other additives shown above are weighed, and then mixed under stirring in solvent C followed by removal of the solvent C, to obtain a desired zwitterionic type ionic liquid/proton donor mixture.

Because the blending ratio (molar ratio) of a zwitterion in an ionic liquid and a proton donor may change depending on the kinds of the zwitterionic type ionic liquid and the proton donor, it is desirable to decide an optimum range as appropriate. Accordingly, a specific blending ratio in a BImC4S/HTFSI mixture synthesized in the Example described later shows merely a suitable blending ratio for a specific combination, to which the present invention is not limited. As for such a suitable range of a blending ratio (molar ratio), as shown in FIG. 2 described later, by measuring a temperature dependency of weight reduction rate of a proton conductor, a range of a blending ratio (molar ration) having weight reduction rate of almost the same as or more than weight reduction rate of a zwitterion alone may be determined. However, as seen in FIG. 2, when a proton donor is present in excess (see the curve of the weight reduction rate of zwitterionic type ionic liquid:proton donor=1:1 (molar ratio)), the proton donor would evaporate as described before. This evaporation would cause the weight reduction rate to begin to gradually decline at around 100° C. However, the proton donor stops evaporation around a temperature exceeding 350° C. (see point P where the above curve intersects with the curves of the weight reduction rate of zwitterionic type ionic liquid in Figure:proton donor=2:1 and 1.5:1 (molar ratio)). Accordingly, the curve of the weight reduction rate of zwitterionic type ionic liquid:proton donor=1:1 overlaps the curves of the rates of weight reduction for zwitterionic type ionic liquid: proton donor=2:1 and 1.5:1 (molar ratio). A zwitterion (BImC4S) that does not show vapor pressure at about 60 to 200° C. which is an operating temperature of a fuel cell begins to reduce its weight around a temperature exceeding 300° C. It is considered that this weight reduction is caused not by evaporation by evaporating pressure, but by thermal decomposition. It is further considered that in a proton conductor (BImC4S/HTFSI mixture) of zwitterionic type ionic liquid: proton donor=2:1 and 1.5:1 (molar ratio), interaction between a zwitterion and a proton donor represses thermal decomposition of the zwitterion, and thus contributes to milder thermal weight reduction rate than that of a zwitterion (BImC4S).

Solvents of a low boiling point such as methanol and ethanol can be used as the solvent C so as to repress evaporation of a zwitterionic type ionic liquid and a proton donor in a subsequent step for solvent removal, but the solvent C is not limited to these solvents. Since a zwitterionic type ionic liquid has comparatively high viscosity, the solvent C may be used to make it less viscous for easier stirring/mixing with a proton donor. Therefore, depending on the viscosity of a zwitterionic type ionic liquid, the zwitterionic type ionic liquid and a proton donor may be stirred and mixed simply.

Methods for removing the solvent C includes, for example, heated vacuum drying, but not limited to.

By observing an expected current in a practical operation of a single fuel cell shown in FIG. 4 of the Example, it can be easily confirmed that the obtained zwitterionic type ionic liquid/proton donor mixture is a proton conductor. This can be also confirmed by measuring ion conductivity as shown in FIG. 3.

The fuel cell according to the present invention has a feature in using the proton conductor of the present invention as described above. It is an object of the present invention to provide a fuel cell that can solve a problem of a complicated and enlarged system caused by installing a system of a humidifying device, a recovering device and a resupplying device that are necessary to keep proton transportation stably in an operation environment of a fuel cell.

The fuel cell using the proton conductor of the present invention containing a zwitterionic type ionic liquid can be applied to a conventionally known fuel cell using a proton conductor such as Nafion (registered trademark) and phosphoric acid, and also can be applied to a proton-exchange membrane fuel cell and a phosphoric acid fuel cell. FIG. 4 shows a single cell structure of a fuel cell using a zwitterionic type ionic liquid which is a proton conductor of the present invention. Such single cell structure is basically similar to a structure of a proton-exchange membrane fuel cell or a phosphoric acid fuel cell.

As shown in FIG. 4, in a fuel cell 1 of the present invention, a matrix 5 for supporting can be impregnated with the proton conductor 3 using a zwitterionic type ionic liquid of the present invention, to be used as an electrolyte membrane 7. The matrix 5 include an inorganic porous material such as silicon carbide (SiC) and silica (SiO) and a membrane of a fluorine-based polymer, a hydrocarbon-based polymer and the like. To the both sides of the electrolyte membrane 7 comprising the matrix 5 impregnated with the proton conductor 3, catalyst layers 9 formed using a platinum (Pt) supported on carbon and the like may be disposed. Further, at outer-side thereof, gas-diffusion layers 11, which promotes diffusion of a fuel gas and air to the catalyst layers 9, may be disposed. The gas-diffusion layers 11 may be further sandwiched between separators 15 having paths 13 for guiding a fuel gas and air. Sealing materials 17 such as silicone rubber and Viton® for preventing hydrogen gas and air from leaking out of the cell may be attached to the outer circumference (periphery) of the side of the catalyst layers 9. As above, the basic structure of a single cell of a fuel cell using a zwitterionic type ionic liquid, that is the ion conductor of the present invention, has been explained roughly, but the present invention is not limited thereto.

EXAMPLE

The present invention will be described below more specifically with referring to working examples.

Example 1

(1) Synthesis and Identification of a Zwitterionic Type Ionic Liquid

In this example, a synthesis example of 1-(-1-butylimidazolio)butane-4-sulfonate (hereinafter, referred to as BImC4S) as a zwitterionic type ionic liquid is given (see FIG. 1).

As shown by a synthesis method in FIG. 1, 21.0 mmol of n-butylimidazole solution in acetone and the equimolar amount of 1,4-butanesultone solution in acetonitrile were mixed at 0° C., then heated to a room temperature and reacted under stirring at room temperature under a nitrogen atmosphere for 5 days. After stopping stirring, organic solvents, as acetone and acetonitrile, were removed by heated vacuum drying, and the residue was washed with acetone to obtain a colorless, clear and viscous zwitterionic type ionic liquid, BImC4S.

The structure of the resultant zwitterionic type ionic liquid was confirmed with $^1$H NMR. In $^1$H NMR, a peak position (chemical shift) and a degree of peak splitting (multiplicity) are different depending on a hydrogen atom-binding site present in the molecule. Peak area intensity is different in proportion to the number of the hydrogen atoms present in the same surrounding (chemically equivalent). The degree of peak splitting (multiplicity) splits into the number obtained by adding 1 to the number of hydrogen atoms binding to the carbon atom adjacent to the carbon atom to which the targeted hydrogen atom is bound. For example, the peak of the hydrogen atom of (i) in the structural formula of the zwitterionic type ionic liquid in FIG. 1 splits into 2+1=3, because the number of the hydrogen atom (hydrogen atom of (ii)) bound to the carbon atom adjacent to the carbon atom, to which the hydrogen atom of (i) is bound, is 2. The peak area intensity (integrated area intensity) corresponding to the hydrogen atom of (i) is 3 (described as "3H"), because 3 equivalent hydrogen atoms are present. Accordingly, the peak corresponding to the hydrogen atom (i) has a multiplicity of 3 and an integrated area intensity of 3H (hereinafter, shown to as (t, 3H). The multiplicity is shown by s=singlet (1 multiplicity), t=triplet (3 multiplicity) and m=multiplicity (4 multiplicity or more)). Specifically, the multiplicity and area intensity of the peak predicted from the structure of BImC4S is (i) (t, 3H), (ii) (m, 2H), (iii) (m, 2H), (iv) (t, 2H), (v) (s, 1H), (vi) and (vii) (s, 2H) [note that because the hydrogen atoms (vi) and (vii) are not equivalent, it is predicted to give two (s, 1H)'s, however, the hydrogen atoms bound to a heterocycle often show one peak as if they were equivalent. In this system, in the molecule of which the structure is known, the peaks of the hydrogen atoms corresponding to (vi) and (vii) of a heterocycle do not split, but show one peak (s, 2H)], (viii) (t, 2H), (ix) (m, 2H), (x) (m, 2H) and (xi) (t, 2H). The chemical shift can be predicted from the molecule of which the structure has been known. The chemical shift, multiplicity and area intensity predicted from the structure are: d=0.85 (t, 3H), 1.2 (m, 2H), 1.7 (m, 2H), 1.0-2.0 (m, 2H), 1.0-2.0 (m, 2H), 2.4 (t, 2H), 4.1-4.2 (t, 2H), 4.1-4.2 (t, 2H), 7.7 (s, 2H) and 9.1 (s, 1H). On the other hand, the observed NMR peaks give 0.84 (t, 3H), 1.19 (m, 2H), 1.47 (m, 2H), 1.72 (m, 2H), 1.83 (m, 2H), 2.39 (t, 2H), 4.11 (t, 2H), 4.15 (t, 2H), 7.73 (s, 2H) and 9.20 (s, 1H), which almost correspond to the predicted values, and thus the synthesis of desired product can be confirmed.

(2) Production of a Zwitterionic Type Ionic Liquid/Protonic Acid Mixture

In this example, the above BImC4S as a zwitterionic type ionic liquid and HTFSI (see FIG. 1 for the structure) as a proton donor were used in the production example.

BImC4S and HTFSI were weighed so as to give a predetermined molar ratio and mixed under stirring in methanol followed by heated vacuum drying, to obtain as a desired product a zwitterionic type ionic liquid (BimC4S)/protonic acid (HTFSI) mixture as a proton conductor.

The ratio of HTFSI and BImC4, [HTFSI]/[BImC4] ([ ] represents number of moles), is preferably 0.5 or more and 1.0 or less, more preferably 0.5 or more and 0.67 or less. A too high mixing ratio of HTFSI would cause the proton conductor to decrease at operation of a fuel cell due to evaporation of HTFSI having vapor pressure (see FIG. 2). In contrast, a too low mixing ratio of HTFSI would bring about insufficient proton conductivity due to low proton concentration in the conductor. As for FIG. 2, explanation thereof is omitted here, as the preparation method of the proton conductor of the present invention has been already described above.

The Arrhenius plot for the ion conductivity of the proton conductor having a ratio of [HTFSI]/[BImC4]=0.5 is shown in FIG. 3. In addition, the temperature dependency (Arrhenius plot) of the ion conductivity of phosphoric acid ($H_3PO_4$) is shown by a solid line in the Figure. The lines for s=0.1, which is the ion conductivity required for an electrolyte of a fuel cell, and s=0.2 and s=0.3, are also shown by dotted or broken lines. It can be seen in FIG. 3 that the BImC4S/HTFSI mixture of the proton conductor obtained in the present Example shows higher ion conductivity than phosphoric acid at a temperature of 160° C. or higher (in the Figure, the temperature at the intersection "X" of the ion conductivity of phosphoric acid and the ion conductivity of the BImC4S/HTFSI mixture of the proton conductor). It can be seen also in FIG. 3 that the proton conductor having a ratio of [HTFSI]/[BImC4]=0.5 can attain the ion conductivity s=0.1 required for an electrolyte of a fuel cell at 140° C. or higher. It has been thus confirmed that the proton conductor obtained in the present Example is sufficiently applicable, without such limitation, to even a proton-exchange membrane fuel cell wherein the operating temperature is limited to 100° C. or lower due to use of water for the proton conductor made by a fluorine-based polymer membrane, not to mention to a phosphoric acid fuel cell. In other words, a conventional proton-exchange membrane fuel cell has been compelled to operate at a low temperature to prevent water from evaporating, though a higher operating temperature gives higher ion conductivity. Since materials constituting a fuel cell that have sufficient thermal resistance at an operating temperature of 140° C. or higher have been already used or developed, the novel ion conductor can be readily applicable to a conventional fuel cell.

Next, a single-cell structure of a fuel cell as shown in FIG. 4 was fabricated using the zwitterionic type ionic liquid (BImC4S)/protonic acid (HTFSI) mixture, which is a proton conductor obtained in the present Example. In the fuel cell 1 of the present Example, a matrix 5 for supporting was impregnated with the proton conductor (BImC4S/HTFSI mixture having a ratio of [HTFSI]/[BImC4]=0.5) 3 containing a zwitterionic type ionic liquid obtained in the present Example, to be used as an electrolyte membrane 7. A SiC porous material was used as the matrix 5. To the both sides of the electrolyte membrane 7 comprising the matrix 5 impregnated with the proton conductor 3, catalyst layers 9 composed of a platinum (Pt) supported on carbon were disposed. Further, at outer-side thereof, gas-diffusion layers 11, which promotes diffusion of a fuel gas and air to the catalyst layers 9, were disposed. The gas-diffusion layers 11 were further sandwiched between separators 15 having paths 13 for guiding a fuel gas and air. Sealing materials 17 were attached to the outer circumference (periphery) of the side of the catalyst layers 9. By observing an expected current in a practical operation of the fabricated single fuel cell, it could be confirmed that the obtained zwitterionic type ionic liquid/proton donor mixture was a proton conductor.

Figure 1:
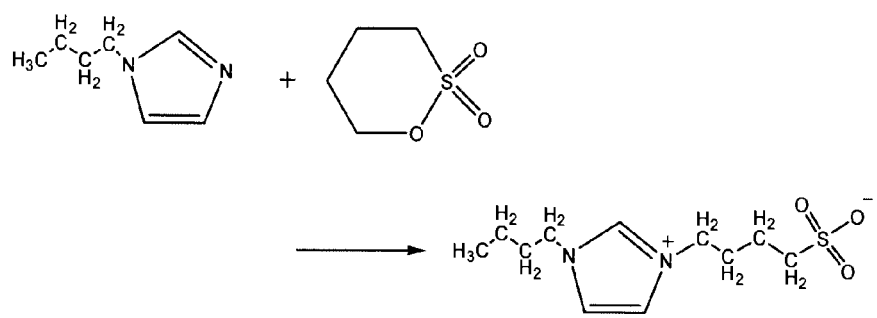
FIG. 1 is a chemical reaction for synthesizing a zwitterionic type ionic liquid (BImC4S) produced in Example 1, a diagram illustrating confirmation of a structure of a zwitterionic type ionic liquid produced in Example 1 using $^1$H NMR, and a diagram illustrating a structure of HTFSI, which is the proton donor used in Example 1.
Figure 1:
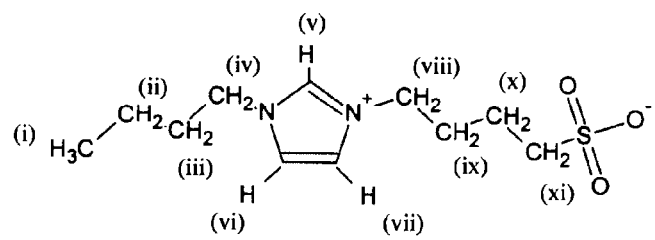
Figure 1:
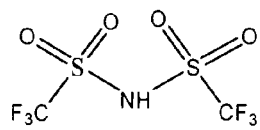
Figure 2:
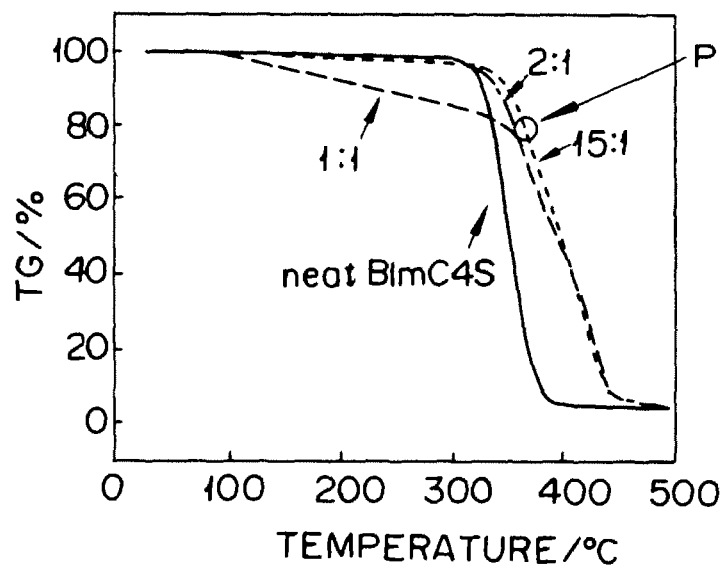
FIG. 2 is a graph showing temperature dependency of a weight reduction rate of a BImC4S/HTFSI mixture, which is the proton conductor produced in Example 1, that is, a graph showing thermogravimetry change (TG/%) versus temperature (° C.). In addition, the curve showing thermogravimetry change of a zwitterionic type ionic liquid (BImC4S) alone is shown by a solid line (neat BImC4S).
Figure 3:
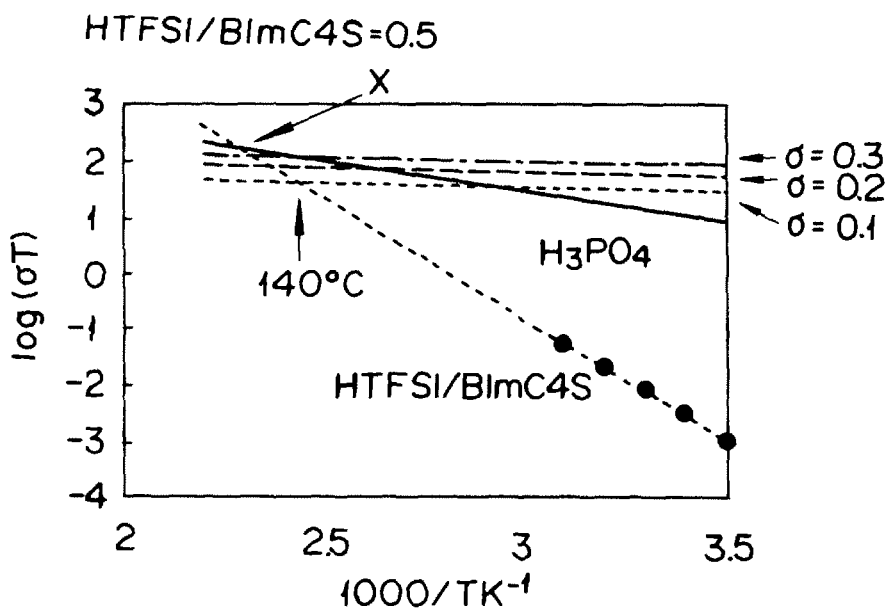
FIG. 3 is a temperature dependency (Arrhenius plot) of ion conductivity of a proton conductor, when the BImC4S/HTFSI mixture, which is the proton conductor produced in Example 1, has a ratio of [HTFSI/BImC4]=0.5.
Figure 4:
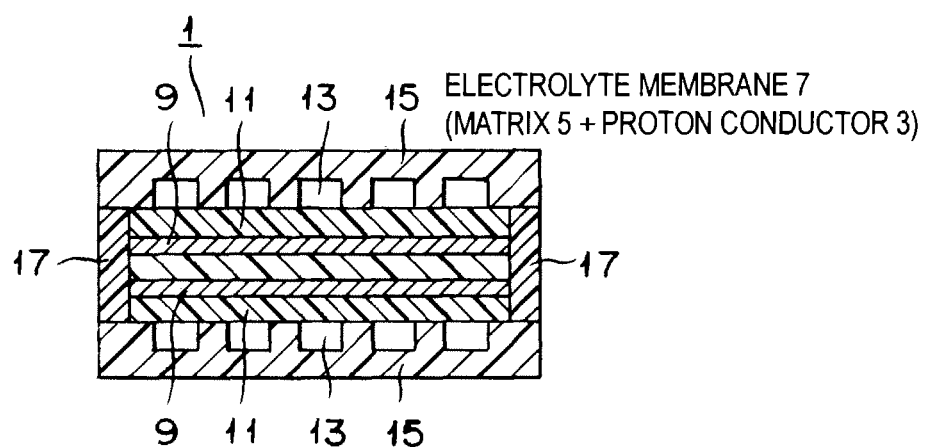
FIG. 4 is a cross-sectional view schematically showing a single cell structure of a fuel cell using a zwitterionic type ionic liquid (BImC4S)/protonic acid (HTFSI) mixture which is a proton conductor obtained in the present Example.

The invention claimed is:

1. A proton conductor comprising an ionic liquid having a zwitterion wherein an anion moiety and a cation moiety coexist in one molecule, and a proton donor,
    wherein the cation moiety of the zwitterion is an onium cation represented by the following structural formula 1:

(Formula 1)

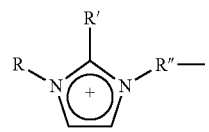

(1)

(wherein R is a hydrogen atom or an alkyl group having 1 to 18 carbon atoms; R' is a hydrogen atom or an alkyl group having 1 to 18 carbon atoms; R" is an alkylene group having 1 to 18 carbon atoms)
    wherein the anion moiety of the zwitterion is selected from the group represented by the following structural formula 2:

(Formula 2)

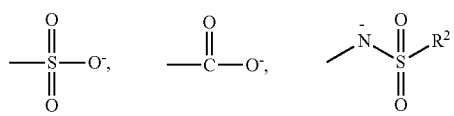

(2)

(wherein $R^2$ is a substituted or unsubstituted monovalent hydrocarbon group, or a fluorocarbon group having 1 to 5 carbon atoms), and wherein the proton donor is selected from the group represented by the following structural formula 3:

(Formula 3)

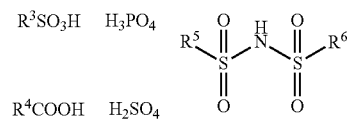

(3)

(wherein $R^3$ is a hydrocarbon group having 1 to 5 carbon atoms or a fluorocarbon group having 1 to 5 carbon atoms; $R^4$ is a hydrocarbon group having 1 to 5 carbon atoms or a fluorocarbon group having 1 to 5 carbon atoms; and $R^5$ and $R^6$ independently are a substituted or unsubstituted monovalent hydrocarbon group or a fluorocarbon group having 1 to 5 carbon atoms), and, wherein the proton donor generates protons in a humid environment.

2. A fuel cell using the proton conductor set forth in claim 1.

3. The proton conductor according to claim 1, wherein the zwitterionic type ionic liquid is obtained by reacting a tertiary amine and an alkylsultone according to the following reaction:

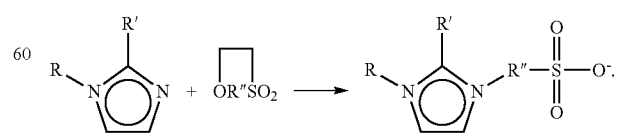

* * * * *